United States Patent [19]

Cincotta

[11] Patent Number: 5,877,183

[45] Date of Patent: Mar. 2, 1999

[54] TREATMENT OF LIPID AND GLUCOSE METABOLISM DISORDERS WITH DOPAMINE AND SEROTONIN AGONISTS

[75] Inventor: Anthony H. Cincotta, Charlestown, Mass.

[73] Assignee: Ergo Research Corporation, Wakefield, R.I.

[21] Appl. No.: 864,885

[22] Filed: Jun. 6, 1997

Related U.S. Application Data

[60] Provisional application No. 60/019,209 Jun. 6, 1996.
[51] Int. Cl.⁶ .................................................. A61K 31/44
[52] U.S. Cl. ........................ 514/288; 514/213; 514/339; 514/250; 514/866; 514/909
[58] Field of Search .................................... 514/288, 213, 514/337, 250, 866, 909

[56] References Cited

U.S. PATENT DOCUMENTS

| | | |
|---|---|---|
| 4,783,469 | 11/1988 | Meier et al. . |
| 4,971,969 | 11/1990 | Carlier et al. . |
| 5,344,832 | 9/1994 | Cincotta et al. . |
| 5,468,755 | 11/1995 | Cincotta et al. . |
| 5,585,347 | 12/1996 | Meier et al. ............................. 514/12 |

OTHER PUBLICATIONS

International Preliminary Examination Report dated Apr. 1, 1998 received in the corresponding PCT application.

*Primary Examiner*—James H. Reamer
*Attorney, Agent, or Firm*—Darby & Darby

[57] ABSTRACT

Provided are methods for the regulation and modification of lipid and glucose metabolism by administering to a subject a dopamine D1 agonist, optionally in combination with a dopamine D2 agonist, an alpha-1 adrenergic antagonist, an alpha-2 adrenergic agonist, or a serotonergic inhibitor, or optionally in combination with a dopamine D2 agonist coadministered with at least one of alpha-1 adrenergic antagonist, an alpha-2 adrenergic agonist, or a serotonergic inhibitor, and further administering the subject a serotonin $5HT_{1b}$ agonist.

21 Claims, 7 Drawing Sheets ics in the lay press as "good" cholesterol. Therefore, therapeutic strategies involve attempts both to reduce plasma LDL and VLDL content (that is, reduce total plasma cholesterol), and to increase the HDL fraction of total plasma cholesterol.
TREATMENT OF LIPID AND GLUCOSE METABOLISM DISORDERS WITH DOPAMINE AND SEROTONIN AGONISTS This application claims priority pursuant to 35 U.S.C. 119 from U.S. Provisional Application Ser. No. 60/019,209 filed Jun. 6, 1996, the entire disclosure of which is hereby incorporated by reference.

FIELD OF THE INVENTION

This invention relates to novel, improved methods for modifying or regulating in a subject (vertebrate animal or human) at least one of body weight, body fat, food consumption, lipid metabolism, and glucose metabolism.

BACKGROUND OF THE INVENTION

Obesity and Lipid Metabolism Disorders—Body Fat Loss

In humans, obesity can be defined as a body weight exceeding 20% of the desirable body weight for individuals of the same sex, height and frame (Salans, L. B., in *Endocrinology & Metabolism*, 2d Ed., McGraw-Hill, New York 1987, pp. 1203–1244; see also, R. H. Williams, *Textbook of Endocrinology*, 1974, pp. 904–916). In other animals (or also in humans) obesity can be determined by body weight patterns correlated with prolactin profiles given that members of a species that are young, lean, and "healthy" (i.e., free of any disorders, not just metabolic disorders) have daily plasma prolactin level profiles that follow a pattern characteristic of the species. This pattern is highly reproducible with a small standard deviation. Members of a species suffering from lipid and/or metabolism disorders, however, have aberrant prolactin profiles that depart from the normal (or healthy subjects') pattern by at least 1 SEM in at least two spaced apart time points or by at least 2 SEM (standard error of the mean) in at least one time point.

Obesity, or excess fat deposits, correlate with and may trigger the onset of various lipid and/or glucose metabolism disorders, e.g. hypertension, Type II diabetes, atherosclerosis, retinopathy etc.

Even in the absence of clinical obesity (according to the above definition) the reduction of body fat stores (notably visceral fat stores) in man, especially on a long-term or permanent basis would be of significant benefit, both cosmetically, physiologically and psychologically.

The reduction of body fat stores in domestic animals (as well as pets), especially on a long-term or permanent basis, would also obviously be of considerable economic benefit to man, particularly since farm animals supply a major portion of man's diet; and the animal fat may end up as de novo fat deposits in man.

Whereas controlled diet and exercise can produce modest results in the reduction of body fat deposits, prior to the cumulative work of the present inventors (including the prior co-pending patent applications and issued U.S. patents referred to below), no truly effective or practical treatment had been found for controlling obesity or other lipid metabolism disorders.

Hyperlipoproteinemia is a condition in which the concentration of one or more of cholesterol- or triglyceride-carrying lipoproteins (such as chylomicrons, very low density lipoproteins ("VLDL"), and low-density lipoproteins ("LDL") in plasma exceeds a normal limit. This upper limit is generally defined as the ninety-fifth percentile of a random population. Elevated levels of these substances have also been positively correlated with atherosclerosis and the often resulting cardiac infarction, or "heart attack", which accounts for approximately half of all deaths in the United States. Strong clinical evidence has been presented which correlates a reduction in plasma lipoprotein concentration with a reduced risk of atherosclerosis (Noma, A., et al., *Atherosclerosis* 49:1, 1983; Illingworth, D. and Conner, W., in *Endocrinology & Metabolism*, McGraw-Hill, New York 1987). Thus, a significant amount of research has been devoted to finding treatment methods which reduce levels of plasma cholesterol and triglycerides. High LDL and/or VLDL accompanied by high triglyceride levels in the blood constitute most important risk factors for atherosclerosis. Reduction of one or both of lipoproteins and triglycerides in the blood would reduce the risk of atherosclerosis and cardiac arrest, or retard their development.

Another subset of the plasma lipoproteins found in vertebrates are high density lipoproteins, HDL ("HDL"). HDL serve to remove free cholesterol from the plasma. A high HDL concentration, as a percentage of total plasma cholesterol, has been associated with a reduced risk of atherosclerosis and heart disease. Thus, HDL are known in the lay press as "good" cholesterol. Therefore, therapeutic strategies involve attempts both to reduce plasma LDL and VLDL content (that is, reduce total plasma cholesterol), and to increase the HDL fraction of total plasma cholesterol. Several lines of research indicate that simply increasing HDL is of benefit even in the absence of LDL or VLDL reduction: Bell, G. P. et al., *Atherosclerosis* 36:47–54, 1980; Fears, R., *Biochem. Pharmacol.* 33:219–228, 1984; Thompson, G., *Br. Heart J.* 51:585–588, 1989; Blackburn, H. *N.E.J.M.* 309:426–428, 1983.

Current therapies for hyperlipoproteinemias include a low fat diet and elimination of aggravating factors such as sedentary lifestyle. If the hyperlipoproteinemia is secondary (i.e., incident to e.g., a deficiency of lipoprotein lipase or LDL receptor, various endocrine pathologies, alcoholism, renal disorders, or hepatic disorders) then control of the underlying disease is also central to treatment. Hyperlipoproteinemias are also treated with drugs, which usually alter the levels of particular components of the total plasma cholesterol, as well as reduce the total plasma lipid component. Among the most recently introduced drugs to treat hyperlipoproteinemia is lovastatin (MEVACOR®) which selectively inhibits an enzyme involved in cholesterol production, 3-hydroxy-3-methylglutaryl coenzyme A (HMG-CoA) reductase. This drug specifically reduces total cholesterol and can cause a modest (5–10%) increase in HDL concentrations. However, benefits from these therapies vary from subject to subject.

Moreover, use of the HMG-CoA enzyme inhibitor is sometimes accompanied by side effects such as liver toxicity, renal myoglobinuria, renal shutdown, and lenticular opacity. The risk of such side effects necessitates close monitoring of the patients (e.g., liver function is tested monthly).

Another drug prescribed against hyperlipoproteinemia is clofibrate. The effectiveness of clofibrate also varies from subject to subject and its use is often accompanied by such side effects as nephrotic syndromes, myalgia, nausea, and abdominal pain.

Type II Diabetes (NIDDM) and Glucose Metabolism Disorders

Type II diabetes, also known as non-insulin dependent diabetes mellitus (NIDDM), is one of the most insidious of the major diseases. NIDDM can strike suddenly or lie undiagnosed for years while attacking the blood vessels and nerves. Individuals suffering from NIDDM, as a group, are far more often afflicted with blindness, heart disease, stroke, kidney disease, hearing loss, gangrene, and impotence. One third of all visits to physicians are occasioned by this disease and its complications, and diabetes and its complications are a leading cause of untimely death in the United States and in the Western world.

NIDDM adversely affects the way the body uses sugars and starches which, during digestion, are converted into glucose. Insulin, a hormone produced by the pancreas, makes the glucose available to the body's cells for energy. In muscle, adipose (fat), and connective tissues, insulin facilitates the entry of glucose into the cells by an action on the cell membranes. The ingested glucose is normally converted in the liver to $CO_2$ and $H_2O$ (50%); to glycogen (5%); and to fat (30–40%), the latter being stored in fat deposits. Fatty acids from the adipose tissues are circulated by the bloodstream, returned to the liver for re-synthesis of triacylglycerol, and metabolized to ketone bodies for utilization by the tissues. The fatty acids are also metabolized by other organs. Fat formation is a major pathway for carbohydrate utilization.

The net effect of insulin is to promote the storage and use of carbohydrates, protein, and fat. Insulin deficiency is a common and serious pathologic condition in man. In insulin-dependent diabetes (IDDM or Type I diabetes) the pancreas produces little or no insulin, and insulin must be injected daily for the survival of the diabetic. In noninsulin-dependent diabetes the pancreas retains the ability to produce insulin and, in fact, may produce higher than normal amounts of insulin, but the amount of insulin is relatively insufficient, or less than fully effective, due to cellular resistance to insulin, i.e. cells do not respond to normal levels of insulin by taking up glucose, amino acids, and fat.

In either form of diabetes, there are widespread abnormalities. In most NIDDM subjects, the fundamental defects to which the abnormalities can be traced are (1) a reduced entry of glucose into various "peripheral" tissues and (2) an increased liberation of glucose into the circulation from the liver. Therefore, there is an extracellular glucose excess and an intracellular glucose deficiency. There is also a decrease in the entry of amino acids into muscle and an increase in lipolysis. Hyperlipoproteinemia is also a complication of diabetes. The cumulative effect of these NIDDM-associated abnormalities over time is severe blood vessel and nerve damage which can lead to blindness and gangrene, among other afflictions.

Other than the methods of the present invention and previous work by the present inventors (discussed below), no effective treatment has been found for controlling either hyperinsulinemia or insulin resistance. Hyperinsulinemia is a higher-than-normal level of insulin in the blood. Insulin resistance can be defined as a state in which a normal amount of insulin produces a subnormal biologic response by cells. In insulin-treated patients with diabetes, insulin resistance is considered to be present whenever the therapeutic dose of insulin exceeds the secretory rate of insulin in normal persons. Insulin resistance is also associated with higher-than-normal levels of insulin i.e. hyperinsulinemia—when normal or elevated levels of blood glucose are present.

Previous Work in This Field

Studies by the present inventors and others have indicated that the naturally occurring annual cycle of body fat stores, pervasive among vertebrates in the wild, reflects the activities of an adjustable central metabolistat that is comprised of circadian hypothalamic neural components, among which are dopaminergic and serotonergic activities. Changes in the phase-relationships of these circadian dopaminergic and serotonergic activities induce seasonal changes in metabolism. These circadian activities can be adjusted by appropriately timed treatments with hormones or neurotransmitter-affecting drugs. In this regard, timed administration of bromocriptine, a sympatholytic dopamine $D_2$ receptor agonist ("$D_2$ agonist") with $\alpha_2$ adrenergic receptor agonist ("$\alpha_2$ agonist") and $\alpha_1$ adrenergic receptor antagonist ("$\alpha_1$ antagonist") activities, as well as serotonin ("5-hydroxytryptamine" or "5HT") inhibiting activities, has been demonstrated to reduce body fat stores in a variety of animals including humans without a concomitant reduction in food consumption. Timed administration of bromocriptine has also been found to reduce hyperinsulinemia, hyperlipidemia, and glucose intolerance.

The present inventors and their co-workers have previously discovered that timed administration (i.e., administration at a time of day when the body, because of circadian neurooscillations, is most responsive to a bioactive agent) of either or both of (i) certain prolactin reducing dopamine ($D_2$) agonists such as bromocriptine and (ii) prolactin-increasing substances such as (a) dopamine antagonists, such as metoclopramide and (b) serotonin agonists and precursors, including by way of non-limiting example 5-hydroxytryptophan reduce body fat stores, obesity, plasma triglycerides, and cholesterol as well as hyperglycemia, hyperinsulinemia, and insulin resistance. This work is disclosed in U.S. Pat. Nos. 4,659,715; 4,749,709; 4,783,469; 5,006,526.

It is preferred to administer the prolactin reducing substances at a first predetermined time of day to effect a decrease in the circulating prolactin levels of the subject to be treated during an interval within the subject's daily prolactin cycle or rhythm when circulating (blood) prolactin levels are low in young, healthy subjects of the same species, thereby causing the prolactin rhythm of the treated subject to approach or to conform to the standard or healthy subjects' prolactin rhythm. It is also preferred to administer the prolactin-increasing substances at a second predetermined time of day to effect an increase in the circulating prolactin levels of the subject to be treated during an interval within the subject's daily prolactin cycle or rhythm when circulating (blood) prolactin levels are high in young healthy subjects of the same species, thereby causing the prolactin rhythm of the treated subject to approach, or conform to, the standard or healthy subjects' prolactin rhythm. Such methods are disclosed in U.S. Pat. Nos. 5,468,755; 5,496,803; 5,344,832; 5,585,347, U.S. Ser. No. 08/456,952, and PCT applications US93/12701 and US95/09061.

It is also known in the art that some of the effects of bromocriptine are supported by endogenous dopamine. (*Ergot Compounds and Brain Functions Neuropsychiatric Aspects: Advances in Biochemical Psychopharmacology.* M. Goldstein et al., Eds. (Raven Press, New York, 1980) vol. 23). Specifically, it has been shown that locomotor stimulation and stereotyped behavior responses to bromocriptine are blocked by depletion of endogenous dopamine in rodents. However, if a $D_1$ dopamine receptor agonist is subsequently provided to dopamine depleted animals, the responsiveness to bromocriptine is restored. Jackson, D. M. et al., *Psychopharmacology* 94:321 (1988)). A similar dopaminergic $D_2$:$D_1$ interaction has been demonstrated in dopaminergic inhibition of feeding behavior. Although these studies confirm the importance of a $D_2:D_1$ interaction in the activation of dopaminergic activities, the increased locomotor activity and decreased feeding response to $D_2:D_1$ agonists is acute and short lived, lasting for only a few hours. (Cooper, S. J. et al., in $D_1:D_2$ *Dopamine Receptor Interactions*, J. Waddington, Ed. (Academic Press, London, 1993) pp. 203–234).

Previous work by third parties with $D_1$ and $D_2$ dopamine agonists in combination has not demonstrated any effects on lipid and glucose metabolism, and has not produced long-term responses of dopaminergic activities. The present inventors discovered that the conjoined administration of a $D_1$ dopamine agonist and a $D_2$ dopamine agonist (or at least one of an $\alpha_1$ antagonist, an $\alpha_2$ agonist and a serotonergic inhibitor) in the morning results in an improvement in one or more of the metabolic indices related to lipid and glucose metabolism when compared to the improvement (if any) provided by administration of a dopamine $D_2$ agonist, such as bromocriptine, administered alone.

The present inventors have now unexpectedly discovered that administration of a $D_1$ or $D_2$ agonist (or both) in the morning (e.g., between the hours of 5:00 and 13:00), combined with administration of a $5HT_{1B}$ receptor subtype agonist ("$5HT_{1B}$ agonist") at night (e.g., between the hours of 17:00 and 0:00) results in a surprising and unexpected reduction in food consumption and body weight. Such administration also results in a decrease in one or more metabolic indices related to lipid and glucose metabolism, such as serum glucose levels, total body fat, and body weight.

The present invention, which utilizes specific $5HT_{1B}$ receptor subtype agonists, provides significant advantages over the administration of 5-HTP to patients. Since the $5HT_{1B}$ agonists act specifically at the $5HT_{1B}$ receptor subtype, side effects associated with a nonspecific increase in serotonin associated with non-specific 5-HTP administration can be avoided.

OBJECTS OF THE INVENTION

It is an object of this invention to provide additional improved methods for reducing in vertebrate subjects (including humans) in need of such treatment at least one of food consumption, body weight, body fat, plasma or blood glucose, and blood insulin.

Another object of this invention is to provide methods for reducing at least one of insulin resistance (impaired glucose tolerance), hyperinsulinemia and hyperglycemia, and glycosylated hemoglobin (including A1C), and abating Type II diabetes or Syndrome X.

A further object is to provide methods for reducing or retarding or arresting atherosclerosis by reducing at least one of hyperlipoproteinemia and elevated blood triglycerides and/or cholesterol.

It is another object of this invention to provide methods for modifying and regulating lipid and glucose metabolism in a manner beneficial to the subject.

It is still another object of the invention to provide methods for modifying and regulating lipid and glucose metabolism to provide effective treatments for obesity or weight reduction.

SUMMARY OF THE INVENTION

It has now been found that at least one of the foregoing objects can be accomplished by (A) administering, in the morning, to a subject in need of such treatment at least one of the following:

(i) a dopamine $D_1$ agonist or a dopamine $D_2$ agonist in conjunction with one agent or agent combination selected from groups (ii) through (iv);

(ii) a dopamine $D_2$ agonist;

(iii) at least one of an adrenergic $\alpha_1$ antagonist, an adrenergic $\alpha_2$ agonist, and a serotonergic inhibitor;

(iv) a dopamine $D_2$ agonist further conjoined with at least one of an adrenergic $\alpha_1$ antagonist, an adrenergic $\alpha_2$ agonist, and a serotonergic inhibitor; and also (B) administering to the subject a $5HT_{1B}$ agonist.

Preferably, the foregoing agents in (i), (ii), (iii) or (iv) above ("conjoined agents") are administered at a predetermined time of day, i.e., within a restricted portion of a 24-hour period, preferably in the morning (i.e. close to the time of light onset). Since the dopamine $D_1$ agonist amplifies the effect of the other agent or agents, the $D_1$ agonist is also preferably administered at about the same time. The $5HT_{1B}$ agonist should be administered at night.

The administration of a dopamine $D_1$ or $D_2$ agonist in the morning and the administration of a $5HT_{1B}$ agonist at night results in substantially augmented, and in fact often synergistic, effects in improvement of one or more metabolic indices related to glucose or lipid metabolism, and thus an improved modification or regulation of at least one of glucose metabolism, lipid metabolism, food consumption, body fat or weight gain.

Where a $D_2$ agonist is employed, it is preferably an ergot alkaloid, most preferably bromocriptine.

In another aspect, the present invention is directed to administering to a subject in the morning a $D_2$ agonist and a $5HT_{1B}$ agonist at night, preferably at or shortly before a subject's bedtime.

It has been found that the additional administration of a $5HT_{1B}$ agonist at night can effect a greater improvement on one or more of the foregoing metabolic indices than administration of only a $D_1$ and/or $D_2$ agonist in the morning.

DETAILED DESCRIPTION OF THE INVENTION

Figure 1:
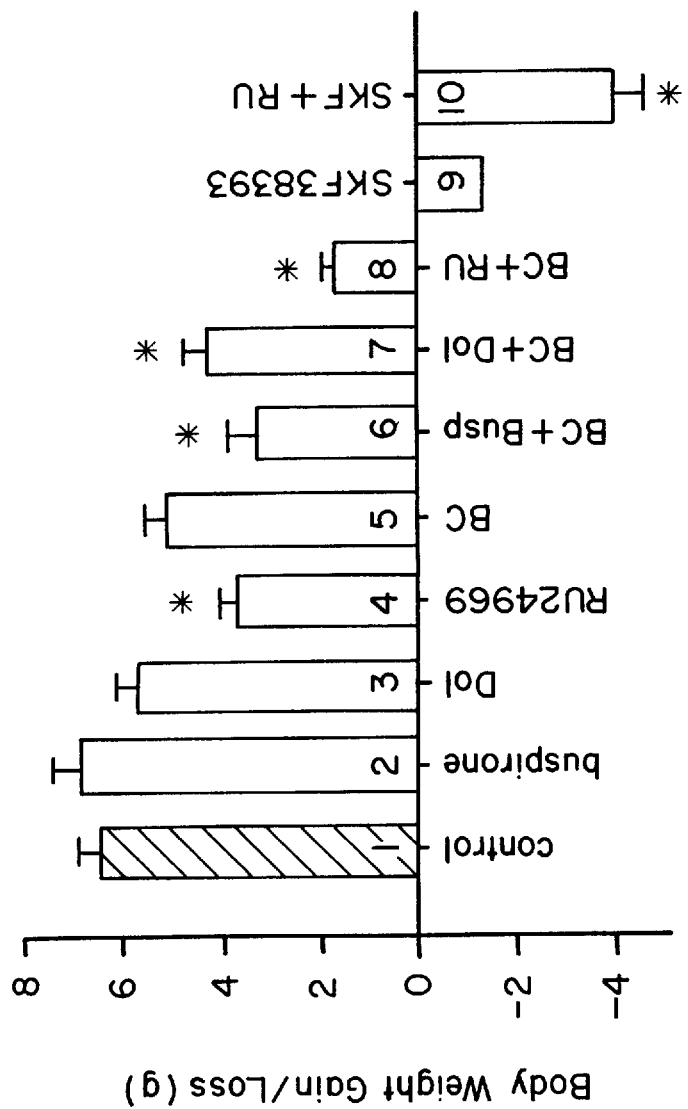
FIG. 1 depicts body weight gain or loss in leptin-deficient mice as a result of treatment with various $D_1$, $D_2$, and 5HT agonists, and combinations thereof.

All literature and patents and patent applications cited herein are incorporated by reference in their entirety. In case of a conflict, the present disclosure including its definitions shall control.

In one embodiment of the method of the present invention, a $D_1$ dopamine agonist is administered, preferably in the morning, and a $5HT_{1B}$ agonist is administered at night, to a subject in need of treatment.

In another embodiment of the method of the present invention, a $D_2$ dopamine agonist is administered, preferably in the morning, and a $5HT_{1B}$ agonist is administered at night, to a subject in need of treatment.

In yet another embodiment of the method of the present invention, a D1 dopamine agonist is administered in conjunction with a $D_2$ dopamine agonist, preferably both are administered in the morning, and a $5HT_{1B}$ agonist is administered at night, to a subject in need of treatment.

In a further embodiment of the method of the present invention, a $D_1$ dopamine agonist is administered in conjunction with a second agent, consisting of at least one of a $D_2$ agonist, an $\alpha_2$ agonist, an $\alpha_1$ antagonist, and a serotonergic inhibitor (or a $D_2$ agonist and at least one of the remaining agents) preferably in the morning, and a $5HT_{1B}$ agonist is administered at night, to a subject in need of treatment.

As used herein and applied to administration of more than one active ingredient the terms "conjoined" or "in conjunction" mean that the subject being thus treated receives a first active agent and also at least one other active agent, but not necessarily within the same formulation or dosage form and not necessarily at the same administration time. For exampe the $D_1$ agonist and $D_2$ agonist or the other agent(s) can be administered at the same time (in the same dosage form or in two or more divided dosage forms) or sequentially at different times and in different dosage forms.

Two subtypes of dopamine receptors, $D_1$ like and $D_2$ like, were identified on the basis of pharmacological and biochemical criteria (see, e.g., Kebabian and Cave, *Nature*, 277:93 (1979)). What is meant by a "$D_1$ dopamine agonist" or "$D_1$ agonist" is a compound which is capable of activating or potentiating $D_1$ dopamine receptors (e.g. $D_1$-like receptors such as $D_1$ and $D_5$ dopamine receptors). See, e.g., Deany et al., *Nature* 347:72–76 (1990), Monsma, et al. *Proc. Natl. Acad. Sci.* USA 87:6723–6727 (1990), Sunahara, et al., *Nature* 347:80 (1990), Zhou, et al., *Nature* 347:76–80 (1990).

Suitable assays for testing compounds for $D_1$ or $D_2$ agonist activity (e.g., receptor binding assays asnd biological functional assays) are well known in the art, see. e.g., Javitch, et al., *Proc. Natl. Acad. Sci.* USA 91:10355 (1994); Piercey, et al., *Eur. J. Pharm.* 317:29 (1996); Paveney, et al., *Eur. J. Pharm.,* 317:175 (1996); Lovenberg, et al., *Eur. J. Pharm.,* 166:111 (1989); Wahs, et al., *Life Sciences,* 31:637 (1982); Seeman, et al., TIPS 15:264 (1994); Brewster, et al., *J. Med. Chem.,* 33:1756 (1990); Sunahara, et al., *Nature,* 347:80 (1990); Chio, et al., *Nature* 343:266 (1990). In one embodiment, the $D_1$ agonist is a selective agonist for the $D_1$ receptor over the $D_2$ receptor (e.g., the compound has a lower $K_i$ or $EC_{50}$ for the $D_1$ receptor than the $D_2$ receptor). In a further embodiment, the $D_1$ agonist is a weak agonist (e.g., $Ki$ or $EC_{50}$ of greater than 1 $\mu$M or 1 mM) or is not a $D_2$ agonist (e.g., $Ki$ or $EC_{50}$ of greater than 10 mM).

The $D_1$ dopamine agonist may be any one or more of those substances known to those skilled in the art that are capable of activating or potentiating $D_1$ dopamine receptors. The $D_1$ agonists that are suitable for use in the present invention include SKF38393, dihydrexidine, SKF 75670, SKF 82957, A77636, A68930, SKF 82526 (fenoldopam), and racemic trans-10, 11-dihydroxy 5, 6, 6a, 7, 8, 12b-hexahydro, and those $D_1$ agonists disclosed in the references cited herein. The preferred $D_1$ dopamine agonist is SKF 38393.

What is meant by a "$D_2$ dopamine agonist" or a "$D_2$ agonist" is a compound which is capable of activating or potentiating $D_2$ dopamine receptors (e.g., $D_2$, $D_2$ short and $D_2$ long receptors, $D_3$, and $D_4$ dopamine receptors). See, e.g., Buntow, et al., *Nature* 3365:783–787 (1988), Del Toso, et al., *EMBO J.* 8:4025–4034 (1989), Giros, et al., *Nature* 342:923–926 (1989), Giaudy, et al., *Proc. Nat. Acad. Sci.* USA 86:9762–66 (1989), and Monsma, et al., *Nature* 342:926–929 (1989). In one embodiment, the $D_2$ agonist is a selective agonist for the $D_2$ receptor over the $D_1$ receptor. In a further embodiment, the $D_2$ agonist is a weak $D_1$ agonist or is not a $D_1$ agonist.

The $D_2$ agonists for use in the present invention can be any one or more of those compounds known to those skilled in the art that are capable of activating or potentiating $D_2$ dopamine receptors. $D_2$ agonists suitable for use in the present invention include benzamides (e.g., sulpiride or raclopride), butyrophenones (e.g., spiroperidol) LY-171555, bromocriptine methane sulfonate (+)-, 2,10,11-trihydroxyapomorphine HBr, R(−)-, lisuride hydrogen maleate, 2-OH—NPA HCl, R(−)-, MDO—NPA HCl R(−), propylnorpamorphine HCl R(−)-(NPA), quinpirole HCl and those $D_2$ agonists recited in the references cited herein.

A preferred class of $D_2$ agonists includes ergot alkaloids such as 2-bromo-alpha-ergocriptine (bromocriptine), dihydroergotamine, 6-methyl 8beta-carbobenzyloxyaminoethyl-10-alpha-ergoline, 8-acylaminoergoline, 6-methyl-8alpha-(N-acyl) amino-9-ergoline, pergolide, lisuride, 6methyl-8alpha-N-phenyl-acetyl)amino-9-ergoline, ergocornine, 9,10-dihydroergocornine, any D-2-halo-6-alkyl-8-substituted ergoline, and D-2-bromo-6-methyl-8-cyanomethylergoline. Of these bromocriptine is most preferred.

Effective amounts of ergot alkaloid for humans and vertebrates when administered alone (not conjoined to a $D_1$ agonist) are typically within the range of 5.0 ug/kg/day to 0.2 mg/kg/day. However, the amount of the $D_1$ agonist, or the $D_2$ agonist, $\alpha_1$ agonist, $\alpha_2$ agonist, serotonin inhibitor, or $5HT_{1B}$ agonist depends on the condition being treated, the route of administration chosen, and the specific activity of the compound used and ultimately will be decided by the attending physician or veterinarian.

In general, effective amounts of $D_2$ agonist for humans and vertebrates are within the range of 5 ug/kg/day to 3.5 mg/kg/day.

Three families of adrenergic receptors have been described in the CNS (i.e., $\alpha_1$, $\alpha_2$, and $\beta$). See, e.g., Goodman & Gilman's *The Pharmacological Basis of Therapeutics,* ed. Hardman, et al. (9th ed. 1996). What is meant by an "adrenergic $\alpha_1$ antagonist" or an "$\alpha_1$ antagonist" is a compound which is capable of blocking activation or down regulating $\alpha_1$ adrenergic receptors, e.g., binding to but not activating or down regulating (see, e.g., Hieble, et al., *J. Med. Chem.,* 38:3416 (1995);).

Suitable assays for testing compounds for $\alpha_1$ or $\alpha_1$ antagonist activity are well known in the art. See, e.g., Marshall, et al., *Br. J. Pharmacol.,* 119:407 (1996); Galligan, J., *J. Pharm. Exp. Ther.,* 264:375 (1993); Silva, et al., *J. Pharm. Exp. Ther.,* 277:872 (1996); Paris, et al., *Mol. Pharm.,* 35:345 (1989); Morrow, et al., *Mol. Pharm.,* 29:321 (1986); Andoin, et al., *Life Sciences,* 43:1805 (1988); Chein, et al., *J. Med. Chem.,* 36:2196 (1993); Piercey, et al., *Eur. J. Pharm.,* 317:29 (1996).

In one embodiment, the $\alpha_1$ antagonist is a selective antagonist for the $\alpha_1$ adrenergic receptor over the $\alpha_2$ adrenergic receptor (e.g., the compound has as lower $K_i$ for the $\alpha_1$ receptor than for the $\alpha_2$ receptor). In another embodiment, the $\alpha_1$ antagonist is a weak $\alpha_2$ antagonist or is not a $\alpha_2$ antagonist.

The $\alpha_1$ antagonists for use in the present invention can be any one or more of those compounds known to those skilled in the art that directly or indirectly block activation of $\alpha_1$ adrenoceptors. The $\alpha_1$ antagonists suitable for use in the present invention include bromocriptine, benoxathin HCl, naftopidil 2HCl, (±)-niguldipine HCl, S(+)-niguldipine HCl, prazosin HCl, doxazosin HCl, spiperone HCl, urapidil HCl, 5-methyl urapidil, WB-4101 HCl, or those $\alpha_1$ antagonists disclosed in the references cited herein.

Effective amounts of $\alpha_1$ antagonist for humans and vertebrates are generally within the range of 0.02 to 0.3 mg/kg/day.

What is meant by an "adrenergic $\alpha_2$ agonist" or a "$\alpha_2$ agonist" is a compound capable of activating or potentiating $\alpha_2$ adrenergic receptors.

In one embodiment, the $\alpha_2$ agonist is a selective agonist for the $\alpha_2$ adrenergic receptor over the $\alpha_1$ adrenergic receptor. In another embodiment, the $\alpha_2$ agonist is a weak $\alpha_1$ agonist or is not an $\alpha_1$ agonist.

The $\alpha_2$ agonists for use in the present invention can be any one or more of those compounds known to those skilled in the art that are capable of activating $\alpha_2$ adrenoceptors. The $\alpha_2$ agonists suitable for use in the present invention include bromocriptine, epinephrine, norepinephrine, agmatine sulfate, p-aminoclonidine HCl, B-HT 920 diHCl, B-HT 933 diHCl, clonidine HCl, guanabenz acetate, p-iodoclonidine HCl, oxymetazoline HCl, UK 14,304, and xylazine HCl or those $\alpha_2$ agonists disclosed in the references cited herein.

Effective amounts of $\alpha_2$ agonist for humans and vertebrates are generally within the range of 1 ug/kg/day to 0.3 mg/kg/day, and preferably between about 100 ug/kg/day and 0.25 mg/kg/day.

The serotonergic inhibitors suitable for use in the present invention include bromocriptine.

Effective amounts of serotonergic inhibitors for humans and vertebrates are generally within the range of 5 ug/kg/day to 0.2 mg/kg/day.

When two (or more) agents are administered in conjunction as disclosed in the Summary of Invention the amount of one or another can be lower than stated above, and even amounts that are subthreshold (when an agent is used singly) can be employed.

What is meant by a "$5HT_{1B}$ agonist" is a compound which is capable of activating or potentiating $5HT_{1B}$ receptors. Suitable assays for testing compound for $5HT_{1B}$ activity are well known in the art. See, e.g., Schoeffer, et al., *Naunyn-Schmiedeberg's Arch. Pharmacol.,* 339:675 (1989); Pauwels, et al., *Eur. J. Pharmacol.,* 290:95 (1995); Pauwels, et al., *Neuropharmacology,* 33:67 (1994); Parker, et al., *J. Neurochemistry,* 60:380 (1993).

In one embodiment, the $5HT_{1A}$ agonist is a selective agonist for the $5HT_{1B}$ receptor over the $5HT_{1A}$ receptor. In another embodiment, the $5HT_{1B}$ agonist is a selective for the $5HT_{1B}$ receptor over the $5HT_2$ receptor.

The $5HT_{1B}$ agonist may be any one or more of those substances known to those skilled in the art that are capable of activating or potentiating $5HT_{1B}$ receptors. Specific $5HT_{1B}$ agonists that are suitable for use in the present invention include RU24969 and CP93,129.

In general, in the practice of the invention, effective amounts of $5HT_{1B}$ agonists for humans and vertebrates are from about 0.01 to about 5.0 mg/kg of body weight.

The dopamine $D_1$ agonist and the dopamine $D_2$ agonist and/or other agent conjoined with the $D_1$ agonist (or with the $D_2$ agonist) as well as the $5HT_{1B}$ agonist may be administered to a subject preferably orally, or parenterally, e.g., by subcutaneous, intravenous or intramuscular injection. Dermal delivery systems, e.g., skin patches, such as ionophoretic patches, as well as suppositories and other well-known systems for administering pharmaceutical agents can also be employed. Sublingual, nasal and other transmucosal modes of administration are also contemplated. Accelerated release compositions, such as those disclosed in U.S. patent application Ser. No. 08/459,021, are preferred.

Each of the $D_2$ agonist, $\alpha_1$ antagonist, $\alpha_2$ agonist, serotonergic inhibitor, and $5HT_{1B}$ agonist are preferably administered at a predetermined time of day. The reason is that the effect of each of these agents on lipid and/or glucose metabolism is time-sensitive, as is explained in more detail for $D_2$ agonists in U.S. Pat. No. 5,585,347 and U.S. Ser. No. 08/456,952, but is also applicable to the $\alpha_1$ antagonists, $\alpha_2$ agonists, serotonergic inhibitors, and $5HT_{1B}$ agonists. The preferred time of administration of $D_1$ agonists, $\alpha_1$ antagonists, $\alpha_2$ agonists, and serotonergic inhibitors is within an interval that results in effective blood levels of the agent(s) at a time during which the standard prolactin levels in healthy subjects of the species to be treated are low. For example in humans standard prolactin levels are low between the hours of 7:00 and 22:00. Accordingly, the predetermined time of administration of one or more of the foregoing agents is between the hours of 5:00 and 13:00, preferably between about 7:00 and about 12:00 or between 07:00 and 09:00. Divided doses can be administered and the schedule of administration can be varied to take into account pharmacokinetic properties of each active agent. Details of administration are given in U.S. Pat. No. 5,585,347 and U.S. Ser. No. 08/456,952 for bromocriptine, but also apply to the $\alpha_1$ antagonists, $\alpha_2$ agonists, and serotonergic inhibitors employed in the present invention.

For mice the preferred time of administration of the first active agent is within 1 hour after light onset. It is further preferred that the administration take place when the subject is neither active nor feeding. The preferred time of administration for the second active agent, a $5HT_{1B}$ agonist, to mice is 11 hours after light onset.

For other vertebrate animals the preferred time of administration of $D_1$, $D_2$, $\alpha_1$, $\alpha_2$, and serotonergic inhibitors can be ascertained by reference to the standard prolactin rhythm for the species of the animal to be treated. The standard prolactin curve can be generated by measuring prolactin in young, healthy members of the species over a 24 hour period. The $D_1$, $D_2$, $\alpha_1$, $\alpha_2$, and serotonergic inhibitors should be administered at a time when prolactin levels are low in young, healthy, lean animals of the same species and sex. See U.S. Pat. No. 5,585,347 and U.S. Ser. No. 08/456, 952.

The administration of the $D_1$ agonist is also preferably timed, i.e. the $D_1$ agonist is also administered at a predetermined time. Because the $D_1$ agonist amplifies the effect of the conjoined agent, it is advantageous to administer the $D_1$ agonist at or about the time of administration of the conjoined agent(s), such that the activity period of the $D_1$ agonist in the bloodstream of the treated subject overlaps (in fact preferably overlaps as much as possible) with the activity period of the conjoined agent. For convenience of administration and in order to promote subject compliance, the $D_1$ agonist can be administered at the same time as the conjoined agent(s).

The $D_1$ agonist may but need not be in the same formulation or dosage form (or form part of the same composition) as the conjoined agent(s). If more than one conjoined agent is administered, the conjoined agents may but need not be in the same formulation or dosage form or form part of the same composition.

In treating human subjects, the $5HT_{1B}$ agonist is preferably administered at night, most preferably at or shortly before a subject's bedtime. In other vertebrate animals, the $5HT_{1B}$ agonist should be administered at or shortly before the time interval during which young, healthy, lean animals of the same species and sex have the highest daily levels of prolactin.

In treating vertebrates, generally, dosages of the $D_1$ and $D_2$ agonists and conjoined agent(s) are typically administered over a period ranging from about 10 days to about 180 days, or longer. Some patients (e.g., patients in particularly poor physical condition, or those of advanced age) may require a longer, or even continuous treatment, e.g., (i) until the condition (e.g., obesity, hyperlipidemia, Syndrome X, or Type II diabetes) is normalized or (ii) for the lifetime of the patient. A treatment duration exceeding six months or even continuous treatment may be desirable even when not required. The $5HT_{1B}$ agonist administration will typically continue for as long as the $D_1$ or $D_2$ agonist administration continues.

At least one of body fat deposits, body weight, plasma or blood glucose, circulating insulin, plasma triglycerides (TG), plasma free fatty acids (FFA), and food consumption of the subject will be reduced as the result of the treatment. Disorders of lipid and glucose metabolism are thereby treated and subjects suffering from such pathologies as hyperphagia, obesity, insulin resistance (impaired glucose tolerance), hyperlipidemia, hyperinsulinemia, and hyperglycemia will exhibit improvement in corresponding metabolic indices.

While appropriately timed administration of certain $D_1$ or $D_2$ agonists (i.e., bromocriptine) alone will produce the effects described above to some degree, these effects are amplified (potentiated) by the conjoined administration of the $D_1$ or $D_2$ agonist agents and $5HT_{1B}$ agonists described in the present invention. In other words, the synergistic effect of the conjoined administration of the $D_1$ or $D_2$ agonist and the conjoined $5HT_{1B}$ agonist produces results that frequently are superior to those experienced through administration of the same amount of a $D_1$ or $D_2$ agonist alone. It should be noted that the present invention permits but does not require each agent to be administered in an amount over the threshold amount (in the absence of a conjoined agent) to improve one or more metabolic indices precisely because of the augmented effect on these indices achieved by conjoined administration according to the present invention.

These and other features of the invention will be better understood by reference to the experiments described in the examples below, which are intended to illustrate, but not in any way limit, the scope of the invention.

EXAMPLE 1

Figure 2:
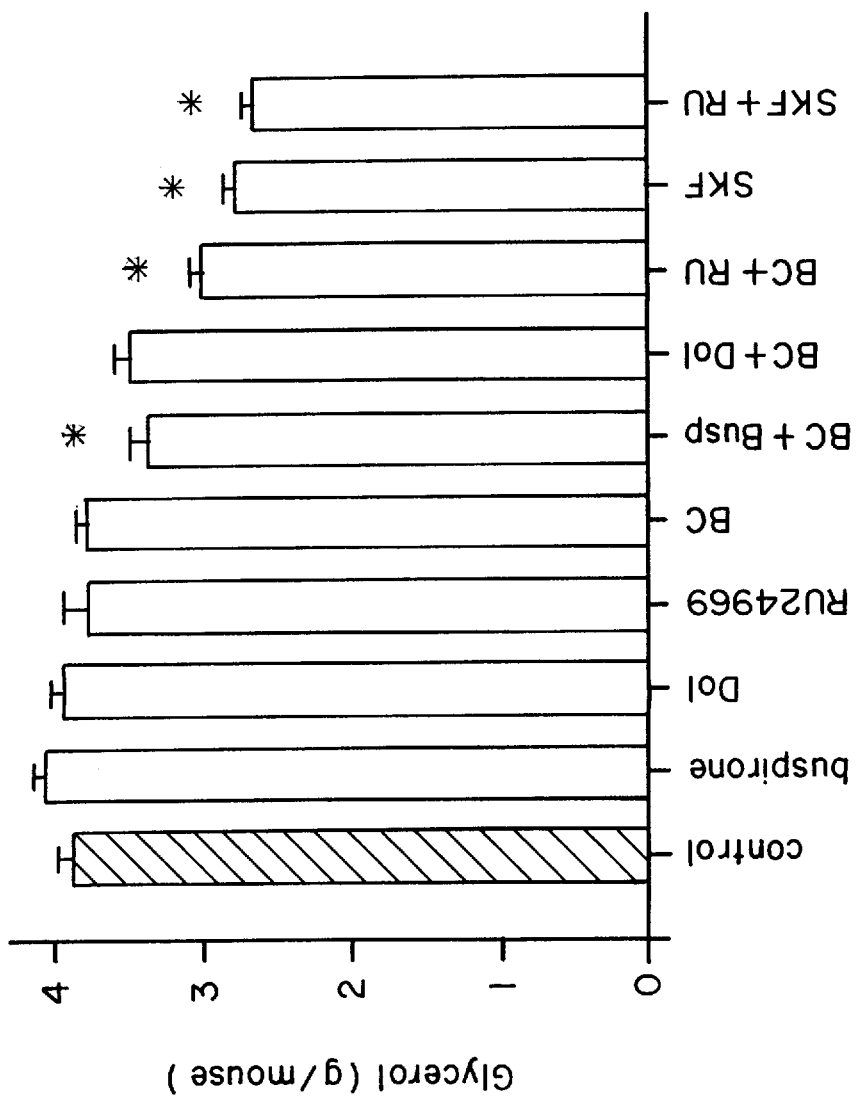
FIG. 2 depicts fat body mass in leptin-deficient mice as a result of treatment with various $D_1$, $D_2$, and 5HT agonists and combinations thereof.
Figure 3:
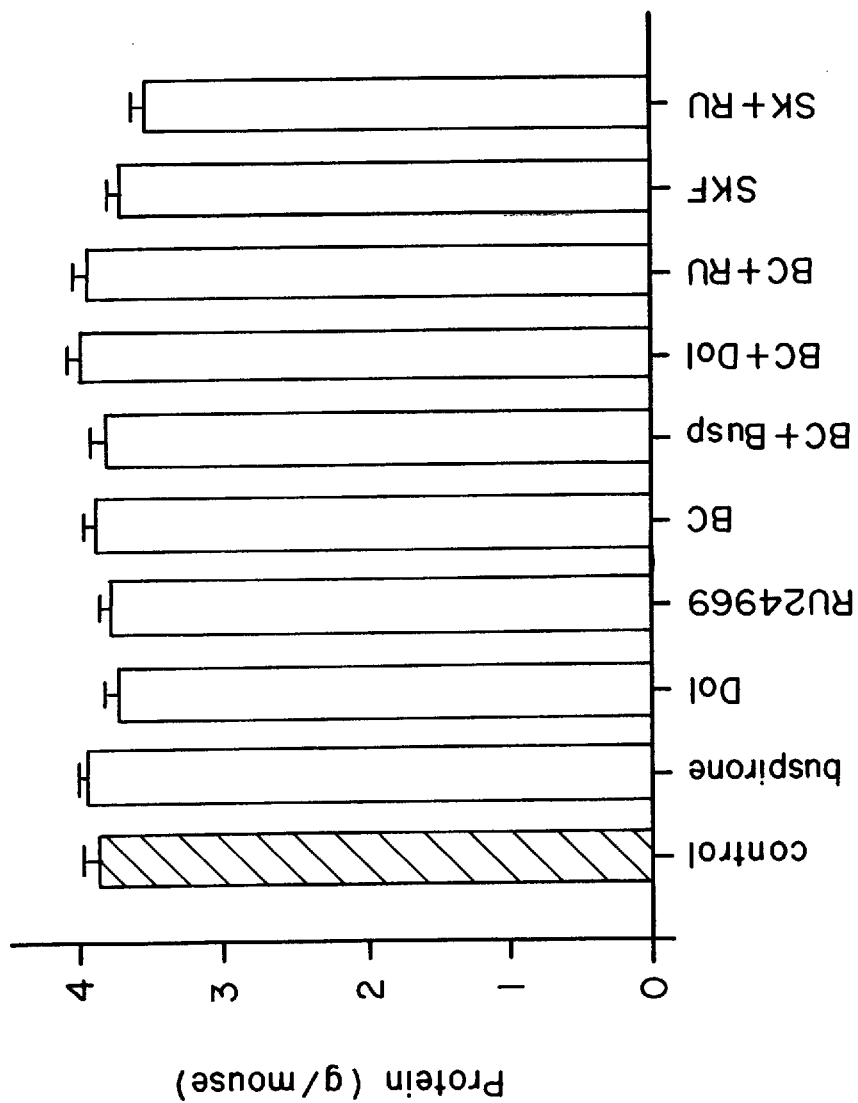
FIG. 3 shows lean body mass in leptin-deficient mice as a result of treatment with various $D_1$, $D_2$, and 5HT agonists and combinations thereof.
Figure 4:
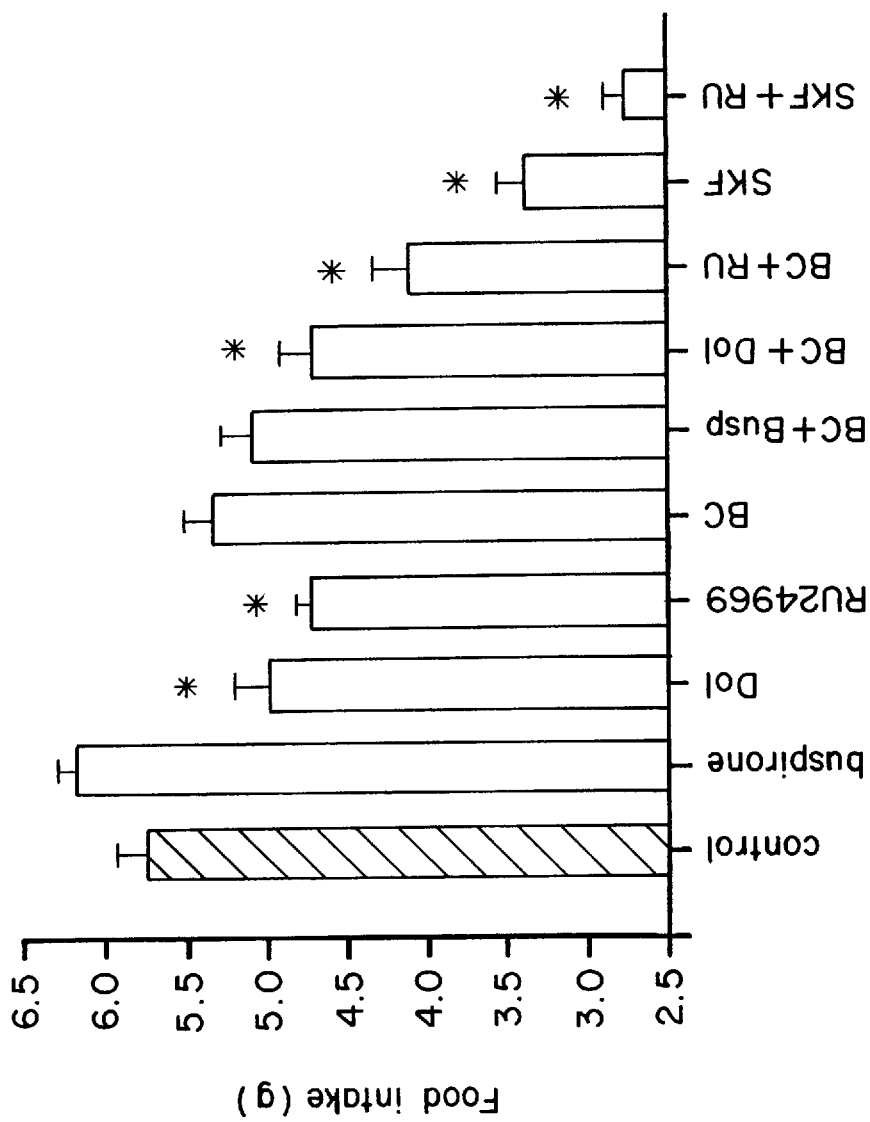
FIG. 4 shows the effect on food consumption over the test period in leptin-deficient mice as a result of treatment with various $D_1$, $D_2$, and 5HT agonists and combinations thereof.
Figure 5:
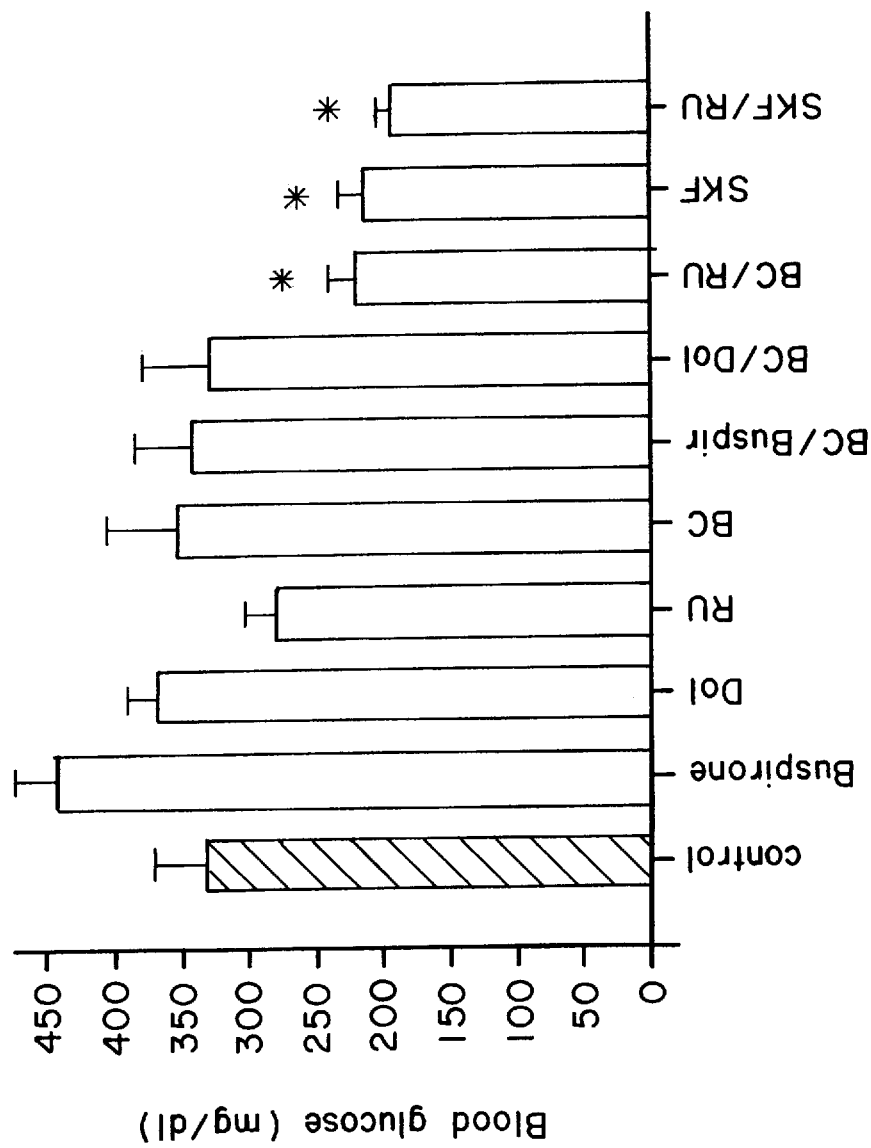
FIG. 5 is a depiction of blood glucose at the end of treatment in leptin-deficient mice as a result of treatment with various $D_1$, $D_2$, and 5HT agonists, and combinations thereof.
Figure 6:
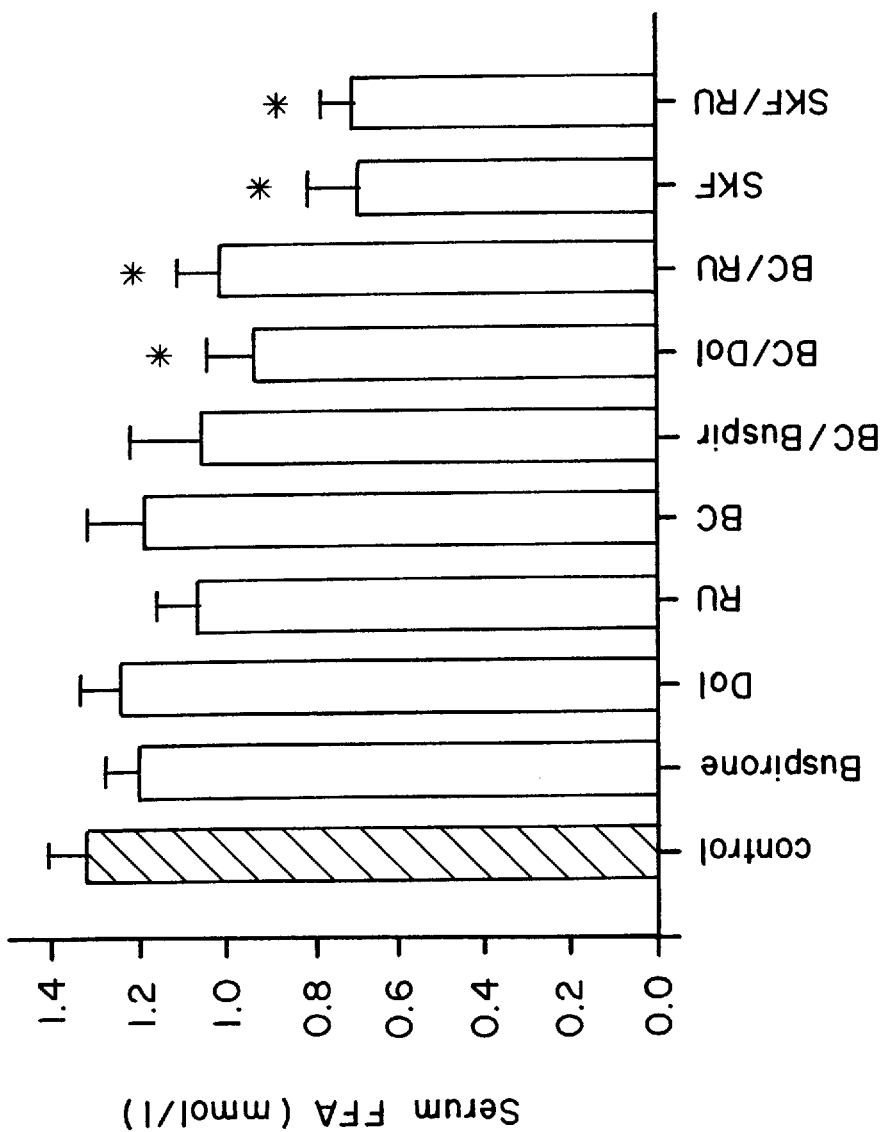
FIG. 6 depicts serum free fatty acids at the end of the treatment period in leptin-deficient mice as a result of treatment with various $D_1$, $D_2$, and 5HT agonists, and combinations thereof.

Different groups (8 mice per group) of 4–8 week old C57BL/6 ob/ob mice (lacking a functional leptin protein) were treated with:
1) vehicle at 1 and 11 hours after light onset (HALO);
2) Buspirone ("Busp"; a $5HT_{1A}$ agonist) (3 mg/kg) at 11 HALO;
3) DOI (a $5HT_2$ agonist) (8 mg/kg) at 11 HALO;
4) RU24969 ("RU") ($5HT_{1B}$ agonist) (3 mg/kg) at 11 HALO;
5) bromocriptine ("BC") (12 mg/kg BW) at 1 HALO;
6) BC (12 mg/kg) at 1 HALO plus Buspirone (3 mg/kg) at 11 HALO;
7) BC (12 mg/kg) at 1 HALO plus DOI (8 mg/kg) at 11 HALO;
8) BC (12 mg/kg) at 1 HALO plus RU (3 mg/kg) at 11 HALO;
9) SKF38393 ("SKF") ($D_1$ agonist) (20mg/kg BW) at 1 HALO; and
10) SKF(20 mg/kg) at 1 HALO plus RU (3 mg/kg) at 11 HALO for two weeks. Animals were held on 12-hour daily photoperiods and allowed to feed ad libitum. Food consumption was monitored daily for 3 days before the initiation of treatment throughout the 14-day treatment period. Animals were sacrificed between 1 and 3 HALO on the day following the final treatment and plasma was collected for the analyses of insulin, glucose, and lipids while the carcasses were solubilized in ethanolic KOH and analyzed for protein and lipid content. Blood glucose was measured with an Accu-Chek Advantage glucose meter (Boehringer). Serum insulin was measured with a radioimmunoassay kit (Linco Research) using rat insulin standards. Total triglycerides and free fatty acids were measured with kits from Sigma Diagnostics and Wako Chemicals, respectively. Body weight gain or loss as a result of treatment is depicted in FIG. 1. Fat body mass is depicted in FIG. 2. Lean body mass is shown in FIG. 3. Food consumption over the test period is shown in FIG. 4. Blood glucose at the end of treatment is shown in FIG. 5. Serum free fatty acids at the end of the treatment period is shown in FIG. 6.

Bromocriptine, Buspirone, and DOI, individually, were ineffective in reducing body weight gain, body fat stores, or food intake. SKF and RU, individually, caused a significant decrease in body weight and food consumption. Relative to controls, the body weight gain in BC/RU treated animals was decreased by about 70%, fat body mass significantly decreased, lean body mass was not significantly decreased, and average daily food consumption decreased significantly, by about 28%. Blood glucose was also significantly decreased relative to controls, as was serum free fatty acids. ($P<0.05$).

Treatment of mice with SKF and RU (SKF/RU) showed the most dramatic results. Food consumption was decreased by 52% and body weight showed a 4 g loss vs. a 6.4 g gain in controls. Body fat stores were decreased 32% compared to controls. Serum glucose was reduced by 42%, and serum free fatty acids were reduced 47%.

Therefore, relative to control mice, the BC/RU and SKF/RU treated animals consumed less food but did not decrease protein mass, while concurrently losing weight and fat.

These data indicate that the interactive effects of BC and RU or SKF and RU effectively reduced hyperphagia, obesity, hyperglycemia, and hyperlipidemia in the ob/ob mouse.

EXAMPLE 2

Different groups of rats were injected intraperitoneally with SKF38393 ("SKF") (10 mg/kg BW) and bromocriptine ("BC") (10 mg/kg BW), SKF and RU24969 ("RU")(3 mg/kg BW), BC and SKF77434 (10 mg/kg BW), or vehicle for 8 days. The BC and SKF were administered at 1 hour after light onset (HALO) and the RU and SKF77434 were administered at 11 HALO. Animals were held on 12-hour daily photoperiods and allowed to feed ad libitum. Food consumption was monitored daily for 3 days before the initiation of treatment throughout the 8-day treatment period. The body weight of the rats at the beginning of the treatment period was from about 385 to 390 grams.

Figure 8:
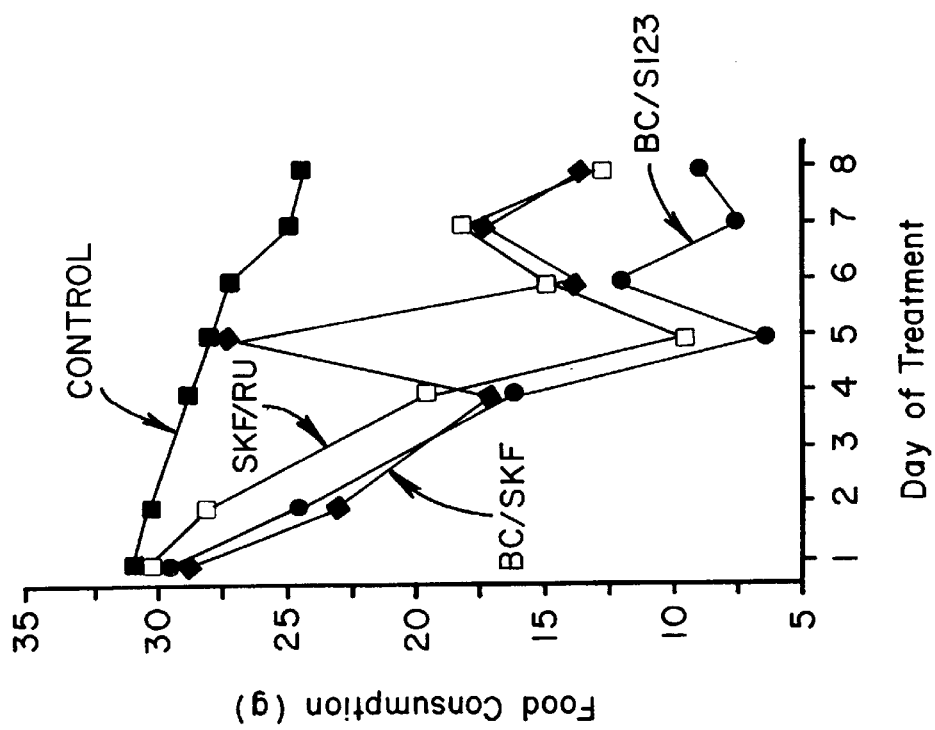
FIG. 8 is a plot of food consumption, in grams, of the rats treated as described in FIG. 7 over the treatment period.
Figure 7:
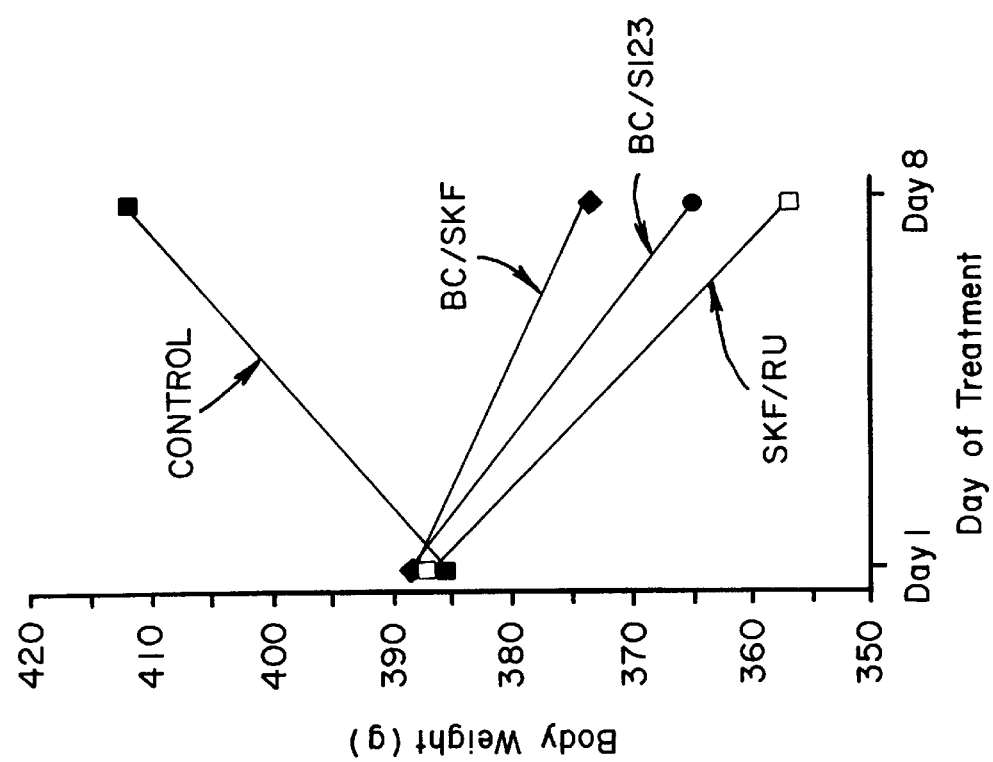
FIG. 7 is a plot of body weight in rats on the first and last day of treatment with a vehicle control, a $D_2$ agonist with a $D_1$ agonist, a $D_2$ agonist with a $5HT_{1B}$ agonist, and a $D_1$ agonist with a $5HT_{1B}$ agonist. Vehicle at 1 and 11 HALO (hours after light onset), BC at 1 HALO plus SKF 38393 at 11 HALO, BC at 1 HALO plus SKF77434 at 11 HALO, or SKF 38393 at 1 HALO plus RU24969 at 11 HALO by injection on body weight in rats during nine days of daily treatment at 1 and 11 hours after light onset.

The combined treatment of bromocriptine and SKF38393 (BC/SKF) resulted in a decrease in food consumption by 29% and a reduction in body weight of 15 grams (3.8%), whereas control rats gained an average of 27 grams over the same 8 day period (FIG. 7). An even more dramatic reduction in body weight was achieved by administration of BC and SKF77434 (a 6.2% weight reduction) and SKF and RU (an 8.2% weight reduction). Similarly, food consumption by BC/SKF treated rats decreased by 29% over the 8 day period, but even greater reductions of 30% (SKF/RU) and 46% (BC/SKF77434) were achieved by administration of D1 or D2 agonist at 1 HALO and a 5HT1B agonist at 11 HALO (FIG. 8). These data indicate that the interactive effects of D1 or D2 agonists 5HT1B agonists given at predetermined times are highly effective in the reduction of obesity and food consumption.

What is claimed is:

1. A method for modifying or regulating at least one of glucose or lipid metabolism disorders, body fat, or body weight which comprises
   (a) administering at a first predetermined time interval to a human or vertebrate animal subject in need of such modification or regulation a member selected from the group consisting of $D_1$ dopamine agonists, $D_2$ dopamine agonists, adrenergic $\alpha_1$ antagonists, adrenergic $\alpha_2$ agonists, and serotonin inhibitors and
   (b) administering at a second predetermined time interval a $5HT_{1B}$ agonist.

2. The method of claim 1 wherein said administrations are effective to decrease at least one of food consumption, body weight, body fat, plasma insulin, plasma glucose, plasma lipid, and plasma lipoprotein.

3. The method of claim 1, wherein said method comprises administering a $D_1$ dopamine agonist.

4. The method of claim 2, wherein said method comprises administering a $D_1$ dopamine agonist.

5. The method of claim 3 wherein the $D_1$ dopamine agonist is SKF38393.

6. The method of claim 1, wherein said method comprises administering a $D_2$ dopamine agonist.

7. The method of claim 2, wherein said method comprises administering a $D_2$ dopamine agonist.

8. The method of claim 6 wherein the $D_2$ dopamine agonist is an ergot alkaloid selected from the group consisting of 2-bromo-alpha-ergocriptine, 6-methyl 8 beta-carbobenzyloxyaminoethyl-10-alpha-ergoline, 8-acylaminoergoline, pergolide, lisuride, 6-methyl-8-alpha-(N-acyl) amino-9-ergoline, 6-methyl-8-alpha-(N-phenylacetyl)amino-9-ergoline, ergocornine, 9,10-dihydroergocornine, and D-2-halo-6-alkyl-8-substituted ergolines, D-2-bromo-6-methyl-8-cyanomethylergoline.

9. The method of claim 8 wherein the ergot alkaloid is bromocriptine.

10. The method of claim 1, wherein said method comprises administering a $D_1$ dopamine agonist and a $D_2$ dopamine agonist.

11. The method of claim 2, wherein said method comprises administering a $D_1$ dopamine agonist and a $D_2$ dopamine agonist.

12. The method of claim 10 which comprises administering the $D_1$ dopamine agonist at about the same time as the $D_2$ dopamine agonist.

13. The method of claim 11 which comprises administering the $D_1$ dopamine agonist at about the same time as the $D_2$ dopamine agonist.

14. A method for treating insulin resistance, obesity, or type II diabetes which comprises
   (a) administering at a first predetermined time interval to a human or vertebrate animal subject in need of such treatment a member selected from the group consisting of $D_1$ dopamine agonists, $D_2$ dopamine agonists, adrenergic $\alpha_1$ antagonists, adrenergic $\alpha_2$ agonists, and serotonin inhibitors; and
   (b) administering at a second predetermined time interval a $5HT_{1B}$ agonist.

15. The method of claim 14, wherein said method comprises treating insulin resistance or type II diabetes.

16. The method of claim 14, wherein said method comprises treating obesity.

17. The method of claim 14, wherein said method comprises administering a $D_1$ dopamine agonist.

18. The method of claim 14, wherein said method comprises administering a $D_2$ dopamine agonist.

19. The method of claim 14, wherein said method comprises administering a $D_1$ dopamine agonist and a $D_2$ dopamine agonist.

20. The method of claim 9, wherein said $D_2$ dopamine agonist is bromocriptine and the $5HT_{1B}$ agonist is RU24969.

21. The method of claim 18, wherein said $D_2$ dopamine agonist is bromocriptine and the $5HT_{1B}$ agonist is RU24969.

* * * * *